US00PP15948P2

(12) United States Plant Patent
Brown, Jr.

(10) Patent No.: US PP15,948 P2
(45) Date of Patent: Sep. 6, 2005

(54) ***TOLMIEA MENZIESII* PLANT NAMED 'COOL GOLD'**

(50) Latin Name: *Tolmiea menziesii*
Varietal Denomination: Cool Gold

(75) Inventor: Kenneth E. Brown, Jr., Tigard, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 81 days.

(21) Appl. No.: 10/884,514
(22) Filed: Jul. 1, 2004
(51) Int. Cl.[7] ..... A01H 5/00
(52) U.S. Cl. ..... Plt./373
(58) Field of Search ..... Plt./373

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Tolmiea menziesii* plant characterized by its yellow green foliage.

1 Drawing Sheet

Botanical classification: *Tolmiea menziesii.*
Variety denomination: 'Cool Gold'.

BACKGROUND OF THE INVENTION

The present invention relates to a new and distinct cultivar of a hardy herbaceous perennial *Tolmiea menziesii*, and known by the cultivar name 'Cool Gold'. *Tolmiea menziesii* is a member of the family Saxifragaceae.

The new cultivar originated as a seedling found by the inventor in his garden in Tigard, Oreg.

SUMMARY OF THE INVENTION

This plant is characterized by the following:

1. Yellow green foliage.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph is of a close up of a two year old *Tolmiea menziesii* 'Cool Gold' growing in an open flat in the greenhouse in late May in Tigard, Oreg.

DETAILED PLANT DESCRIPTION

The following is a detailed description of the new *Tolmiea menziesii* based on observations of three-year-old plants grown in the garden in shade and in the greenhouse in Canby, Oreg. The color descriptions are all based on The Royal Horticultural Society Colour Chart.

Botanical classification: *Tolmiea menziesii.*
Variety denomination: 'Cool Gold'.
Plant:
- *Type.*—Herbaceous perennial.
- *Hardiness.*—USDA Zones 7 to 8.

- *Form.*—Spreading from a thick underground rootstock.
- *Size.*—50 cm wide and 30 cm. high.

Basal foliage: With adventitious buds in the sinuses, typical of the genus.
- *Type.*—Simple.
- *Arrangement.*—Basal.
- *Shape.*—Ovate to cordate.
- *Lobing.*—5 to 7 shallow.
- *Margins.*—Irregularly toothed.
- *Venation.*—Palmate.
- *Apex.*—Acute.
- *Base.*—Cordate, often overlapping.
- *Blade length.*—10.4 cm.
- *Blade width.*—9 cm.
- *Texture.*—Thin, rough.
- *Aspect.*—Matte.
- *Surface.*—Glandular pubescent.
- *Petiole length.*—19.5 cm.
- *Petiole vestiture.*—Glandular pubescent.
- *Petiole color.*—Yellow Green 144B.
- *Leaf color.*—Spring and new growth abaxial — Yellow Green 154D darkening to Yellow Green 145C and then to Yellow Green 144A and B. Spring adaxial — Closest to Yellow Green 145B. Summer abaxial — Yellow Green 144A and B. Summer adaxial — Closest to Yellow Green 147D.

Inflorescence: Typical of the species except for its stem color.
- *Type.*—Raceme.
- *Flower number.*—60 per raceme.
- *Bloom period.*—May to June.
- *Peduncle.*—With 4–6 cauline leaves which are smaller and more lobed than the basal leaves. Height — 59 cm. Width — 3 mm. at the widest point. Color — Yellow Green 144B. Texture — Glandular pubescent.
- *Pedicel.*—Length — 0.45 cm. Texture — Glandular pubescent. Color — Brown, Greyed Orange 165A.
- *Lastingness.*—A raceme blooms for about 3 weeks.

Flower bud:
- *Size.*—0.6 cm deep and 0.25 cm wide.
- *Description.*—Ovoid, downfacing until open.
- *Color.*—Red Brown, Greyed Purple 184A.

Flower:
- *Type.*—Perfect, actinomorphic, sepals petaloid.

*Shape.*—Campanulate.
*Flower size.*—1 cm wide and 1.2 cm deep including stamens and narrow reflexed petals.
*Petal number.*—4.
*Petal shape.*—Linear, reflexed.
*Petal size.*—6 mm long and 0.04 mm. wide.
*Petal color.*—Greyed Purple 184A.
*Calyx.*—5 lobed, petaloid, parted ⅓ to base, reflexed.
*Calyx color.*—Greyed Purple 184A fading to Greyed Orange 177A.
*Calyx size.*—1.1 cm deep and 0.8 cm wide where lobes reflex. Tube is 3 mm wide.
*Stamens.*—3, conspicuously exerted.
*Anthers undehisced.*—Orange 28C.
*Pollen color.*—Yellow Orange 14C.
*Pistil.*—Yellow Green 154C suffused with Greyed Purple 184B, 8 mm long.
*Fragrance.*—Faint.

Fruit:
*Type.*—A one-celled capsule, beak-like, composed of two equal parts.
*Size.*—0.8 cm long.
*Color.*—Brown 200C.

Seeds:
*Color.*—Brown 200A.
*Shape.*—Minute, oval, 1 mm long.
*Fertility.*—Fertile.

Pest and disease resistance: This new cultivar shows good powdery mildew tolerance, the main problem for *Tolmiea menziesii*. Rust, anthracnose, and mealy bug are other potential disease problems. None have been observed on this new cultivar.

COMPARISONS WITH SIMILAR *TOLMIEA MENZIESII*

Compared with *Tolmiea menziesii* 'Taff's Gold', an unpatented plant, *Tolmiea menziesii* 'Cool Gold' has a clean gold leaf rather than a variegated or mottled gold leaf.

Compared to the species, *Tolmiea menziesii*, this new cultivar has yellow green rather than lime green foliage.

I claim:

1. A new and distinct cultivar of *Tolmiea menziesii* plant, as illustrated and described herein, characterized by its yellow green foliage.

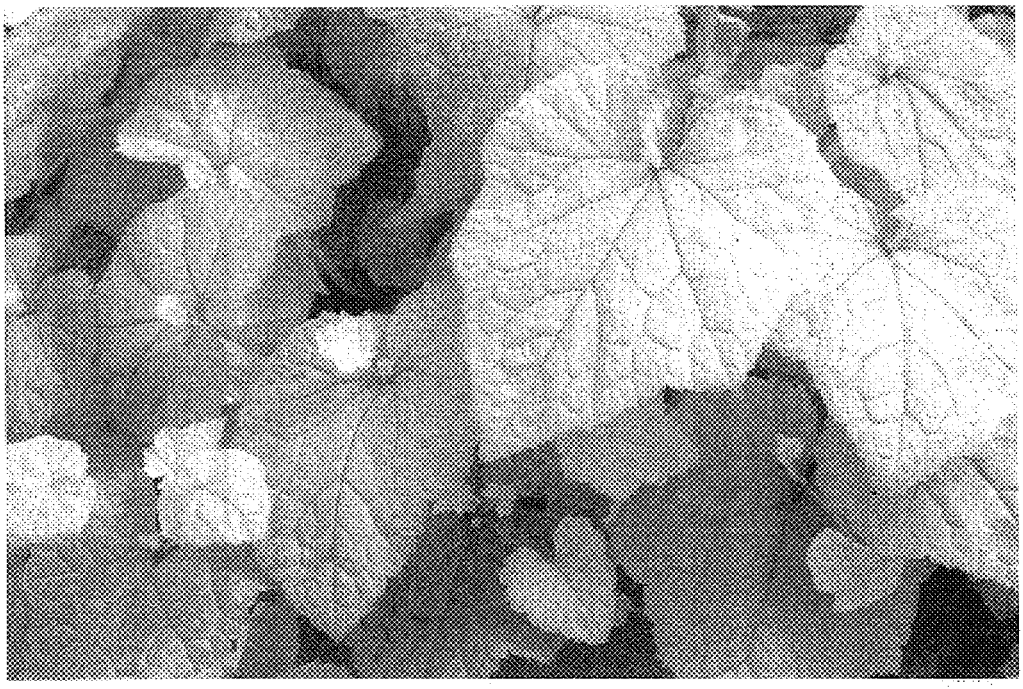

* * * * *